(12) United States Patent
Young

(10) Patent No.: US 11,980,304 B2
(45) Date of Patent: *May 14, 2024

(54) METHOD OF DRYING BOTANICALS

(71) Applicant: Eric Young, Bellingham, WA (US)

(72) Inventor: Eric Young, Bellingham, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/541,724

(22) Filed: Dec. 3, 2021

(65) Prior Publication Data

US 2022/0088101 A1 Mar. 24, 2022

Related U.S. Application Data

(60) Division of application No. 16/796,031, filed on Feb. 20, 2020, now Pat. No. 11,191,797, which is a continuation of application No. 16/376,735, filed on Apr. 5, 2019, now Pat. No. 10,639,340.

(60) Provisional application No. 62/686,424, filed on Jun. 18, 2018.

(51) Int. Cl.

| *A61K 36/00* | (2006.01) |
| *A47G 1/20* | (2006.01) |
| *A61K 36/185* | (2006.01) |
| *F16B 23/00* | (2006.01) |
| *A61K 9/20* | (2006.01) |
| *A61K 9/48* | (2006.01) |

(52) U.S. Cl.
CPC .............. *A47G 1/20* (2013.01); *A61K 36/185* (2013.01); *F16B 23/0023* (2013.01); *A61K 9/20* (2013.01); *A61K 9/48* (2013.01); *A61K 2236/17* (2013.01); *A61K 2236/33* (2013.01); *A61K 2236/37* (2013.01); *A61K 2236/51* (2013.01)

(58) Field of Classification Search
CPC ................................................ A61K 2236/51
See application file for complete search history.

(56) References Cited

U.S. PATENT DOCUMENTS

| 2,278,472 | A | 4/1942 | Musher |
| 3,078,586 | A | 2/1963 | Rey |
| 3,199,217 | A | 8/1965 | Oldenkamp et al. |
| 3,230,633 | A | 1/1966 | Hamilton |
| 3,376,652 | A | 4/1968 | Hernandez, Jr. |
| 4,312,134 | A | 1/1982 | Strausser |
| 4,612,200 | A | 9/1986 | Sato |
| 4,780,964 | A | 11/1988 | Thompson, Sr. |
| 5,656,343 | A | 8/1997 | Baker |
| 6,935,049 | B2 | 8/2005 | Alstat |
| 9,199,960 | B2 | 12/2015 | Ferri |
| 9,351,953 | B2 | 5/2016 | Stodola |
| 9,459,044 | B1 | 10/2016 | Haddock et al. |
| 9,730,911 | B2 | 8/2017 | Verzura et al. |
| 9,739,532 | B2 | 8/2017 | Baugh et al. |
| 10,639,340 | B2 | 5/2020 | Young |
| 11,243,028 | B2 | 2/2022 | Baughman et al. |
| 2003/0078266 | A1 | 4/2003 | Kararli et al. |
| 2005/0144804 | A1 | 7/2005 | Alstat |
| 2006/0051731 | A1 | 3/2006 | Ho et al. |
| 2009/0324586 | A1 | 12/2009 | Tchessalov et al. |
| 2011/0247234 | A1 | 10/2011 | Friess et al. |
| 2015/0258142 | A1 | 9/2015 | Dhanaraj et al. |
| 2016/0000843 | A1 | 1/2016 | Lowe et al. |
| 2016/0245588 | A1 | 8/2016 | Baugh et al. |
| 2017/0196923 | A1 | 7/2017 | Moore |
| 2017/0202895 | A1 | 7/2017 | Hugh |
| 2017/0202896 | A1 | 7/2017 | Hugh |
| 2017/0252384 | A1 | 9/2017 | Goldner |
| 2017/0273349 | A1 | 9/2017 | Moore |
| 2017/0274027 | A1 | 9/2017 | Moore |
| 2018/0008656 | A1 | 1/2018 | Watts et al. |
| 2018/0110816 | A1 | 4/2018 | Suh et al. |
| 2018/0125905 | A1 | 5/2018 | Letzel et al. |
| 2018/0296616 | A1 | 10/2018 | Rivas |
| 2018/0296617 | A1 | 10/2018 | Rivas |
| 2018/0306763 | A1 | 10/2018 | Brucker et al. |
| 2018/0325972 | A1 | 11/2018 | Moore |
| 2020/0188462 | A1 | 6/2020 | Young |
| 2020/0230188 | A1 | 7/2020 | Young |

FOREIGN PATENT DOCUMENTS

| CA | 2020360 A1 | 1/1992 |
| CN | 104288227 A | 1/2015 |
| CN | 105379860 A | 3/2016 |
| CN | 106173079 A | 12/2016 |
| CN | 106857895 A | 6/2017 |
| CN | 107821699 A | 3/2018 |
| CN | 105166133 B | 9/2018 |

(Continued)

OTHER PUBLICATIONS

Written Opinion of the International Searching Authority for International Application No. PCT/US2019/061412 dated Feb. 25, 2020 (6 pages).

CannaFreeze, "CO2 Trimming and Freeze Drying: Crop to Cure in 24 Hours" dated Nov. 9, 2017 and retrieved on Oct. 30, 2023 from <https://www.leafly.com/news/industry/crop-cure-24-hours> (7 pages).

Hudson Valley Lyomac, "Freeze Dryers Made in the USA" retrieved on Oct. 30, 2023 from <http://www.hudsonvalleylyomac.com/uploads/4/7/4/9/47491041/cannabis_420_freeze_dryer_050416.pdf> (2 pages).

(Continued)

*Primary Examiner* — Qiuwen Mi

(74) *Attorney, Agent, or Firm* — KW Law, LLP

(57) ABSTRACT

A method for drying to increase the useful life of botanicals and shorten the time to market after harvest of the botanicals. The method may include flash freezing the botanicals, at a desired optimal temperature range, soon after harvest. The method may include storing the frozen botanicals indefinitely prior to drying. The method may include drying the frozen botanicals using a lyophilizer at a desired optimal temperature and pressure.

9 Claims, 4 Drawing Sheets

(56) References Cited

FOREIGN PATENT DOCUMENTS

| | | | |
|---|---|---|---|
| JP | 2017535539 A | * | 11/2017 |
| KR | 19990039467 A | | 6/1999 |
| WO | 2012132590 A1 | | 10/2012 |
| WO | 2016064987 A1 | | 4/2016 |
| WO | 2016123475 A1 | | 8/2016 |
| WO | 2016131809 A1 | | 8/2016 |
| WO | 2016171997 A2 | | 10/2016 |
| WO | 2017184642 A1 | | 10/2017 |
| WO | 2018195562 A1 | | 10/2018 |
| WO | 2018218148 A1 | | 11/2018 |
| WO | 2019008088 A1 | | 1/2019 |

OTHER PUBLICATIONS

Scitek Australia Pty Ltd, "Freeze Drying—Medicinal Cannabis Production" retrieved on Oct. 30, 2023 from <https://medicinalcannabisproduction.com.au/cannabisfreeze-drying> (4 pages).

Sondles, Scott, "Guide to Preserving Terpenes" dated Feb. 14, 2017 and retrieved on Oct. 30, 2023 from <https://linkedin.com/pulse/guide-preserving-terpenes-scott-sondles> (4 pages).

Dhydra Technologies, "Technology" webpage retrieved on Oct. 30, 2023 from <https://www.dhydratech.com/technology> (8 pages).

Harter, "Cabinet dryer for cannabis" retrieved on Oct. 30, 2023 from <https://making.com/equipment/cabinet-dryer-for-cannabis/> (2 pages).

EnWave Corporation, "EnWave Expands Agreement with Tilray Providing for Cannabis Drying in Portugal", dated Feb. 27, 2018 and retrieved on Oct. 30, 2023 from <https://www.globenewswire.com/news-release/2018/02/27/1396112/0/en/EnWave-Expands-Agreement-with-Tilray-Providing-for-Cannabis-Drying-in-Portugal.html> (2 pages).

EnWave Corporation, "What is REV?" retrieved on Oct. 30, 2023 from <https://www.enwave.net/about/rev/> (4 pages).

Antal et al., "Effects of freeze drying on retention of essential oils, changes in glandular trichomes of lemon balm leaves" International Food Research Journal 21 (1): 387-394 (2014) retrieved on Oct. 30, 2023 from <http://www.ifrj.upm.edu.my> (8 pages).

* cited by examiner

METHOD OF DRYING BOTANICALS

CROSS-REFERENCE TO RELATED APPLICATIONS

The present application is a continuation of U.S. patent application Ser. No. 16/796,031 filed on Feb. 20, 2020 and issued as U.S. Pat. No. 11,191,797, which is a continuation of U.S. patent application Ser. No. 16/376,735 filed on Apr. 5, 2019 and issued as U.S. Pat. No. 10,639,340, which claims priority from U.S. Provisional Patent Application 62/686,424 filed on Jun. 18, 2018. The entire disclosure of each of the aforementioned applications is incorporated herein by reference for any purpose.

BACKGROUND

The present disclosure relates generally to processing botanical items. In particular, methods of drying the botanical items are described.

Conventional techniques for drying botanicals involve slowly drying the harvested botanicals by hanging them in a cool, dry room for several weeks. This process leads to quicker degradation of the appearance and compounds in the botanical. Once the botanical is dry, trimming is difficult. Where the botanical is cannabis, the leaves are generally considered useless and are discarded.

Thus, there exists a need for drying that improves upon and advance the design of known method for processing botanicals, which also includes hemps and cannabis. Examples of new and useful drying methods relevant to the needs of existing in the field are discussed below.

SUMMARY

The methods discussed below dramatically improve the overall appearance, quality, and shelf life of dried botanicals, while decreasing the drying time. According to one aspect of the invention, the improved dried botanical is produced by flash freezing a harvested botanical until the moisture content is solidified. The frozen botanical is dried by sublimating the solidified moisture content to a gas, while continuously removing the gas from the botanical. The resulting dried botanical generally maintains its original volumetric dimensions and maintains its usability for an extended period of time. The botanical can then be placed in a sealed container for future use. The removed gas can be converted to liquid form comprising of water and terpene oil, wherein the lighter terpene oil is separated from the heavier water and collected.

According to another aspect of the invention, the dried botanical may have its oil extracted therefrom. The extracted oil can be stored in capsules or converted into pill form.

According to further aspect of the invention, the dried botanical may be trimmed to form particles, and the trimmed particles can be packed into cylindrical containers for future use. Additionally, the dried botanical can be converted into a powder and packed into cylindrical containers.

According to a still further aspect of the invention, leaves from a botanical are flash frozen and are dried by sublimating solidified moisture from the frozen leaves. The leaves are mulched either prior to being frozen or after being dried, and the resulting mulched leaves may be packed into cylindrical containers for future use.

BRIEF DESCRIPTION

DETAILED DESCRIPTION

The disclosed methods will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, a variety of methods are provided. Related features in the examples may be identical, similar, or dissimilar in difference examples. For the sake of brevity, related features will not be redundantly explained in each example. Instead, the use of related features names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

Figure 1:
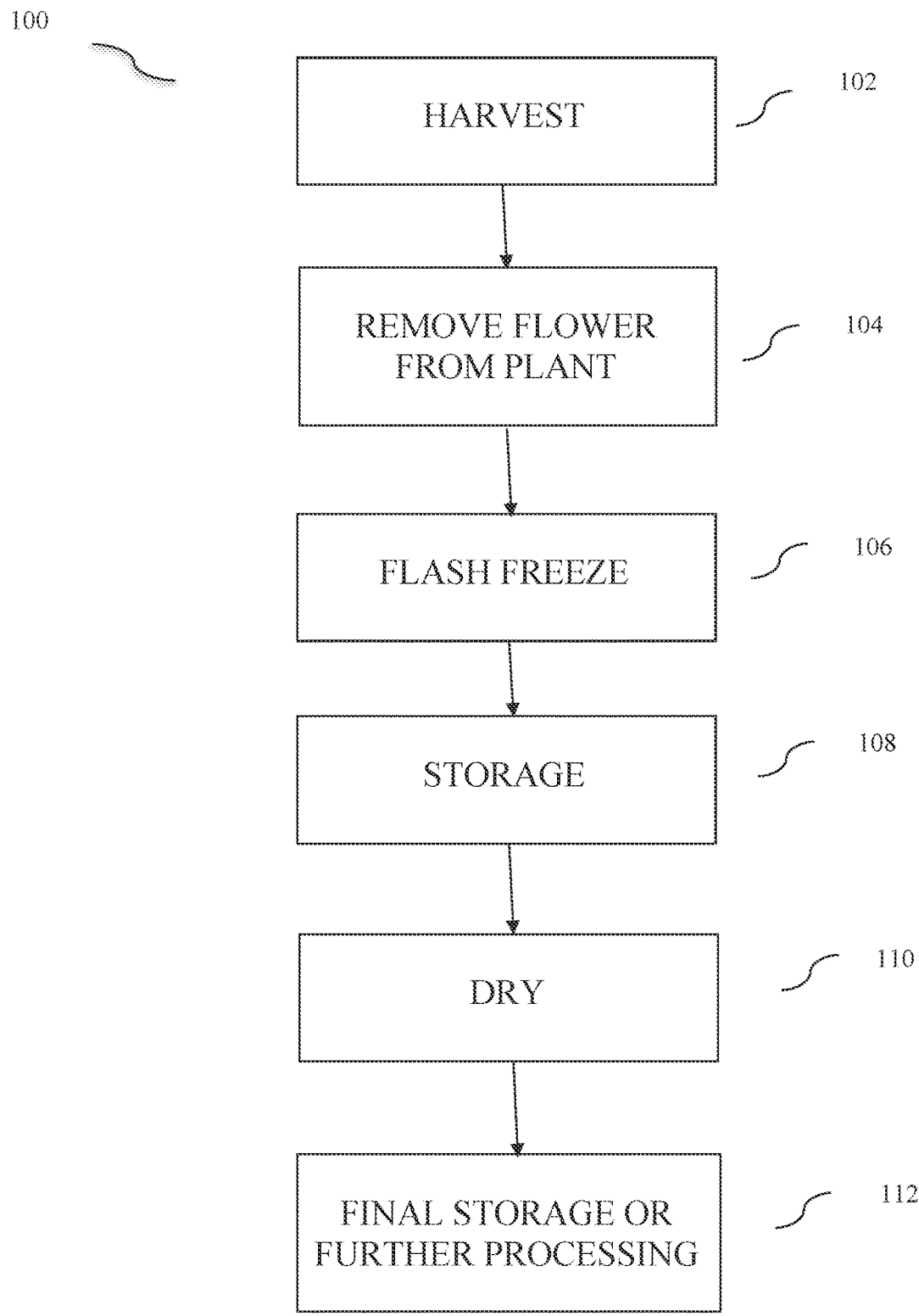
FIG. 1 is a flow chart summarizing a method of drying botanicals, according to an embodiment.

With reference to FIG. 1, one method of 100 of drying botanicals, will now be described. Within hours of harvesting 102 the botanical, it is placed in a freezer, ideally within one hour. For cannabis or hemp processing, it is desirable to remove the flower from the plant 104 and place only the flower in the freezer. In other embodiments, the whole plant may be directly placed in the freezer. Alternatively, the flowers can be removed from the whole plants at later steps of method 100. For each step of flash freezing 106, the freezer should be as cold as possible, with the current range being between −10 degrees Fahrenheit and at least −60 degrees Fahrenheit. The lower temperature insures the botanical freezes as quickly as possible for best preservation. The botanical can then be stored 108 in this frozen state indefinitely until the botanical is needed. After removal from frozen storage, the frozen botanical is dried 110. This process includes placing the botanical in a drying machine, such as a lyophilizer which is generally composed of a vacuum chamber and a vacuum pump. Once the botanicals are placed in the vacuum chamber, the drying machine will lower the air pressure in the chamber and cycle the temperature. This process will allow the botanical to reach the triple point, where the frozen water molecules in the botanical will be sublimated or vaporized and turned into a gas. The machine removes the gas from the vacuum chamber using the vacuum pump, wherein the removed gas is converted to a liquid form comprising of water and terpene oil which is lighter in weight, and the terpene oil is then collected using standard oil water separating procedures. The botanical is then removed, being dry and fully intact and placed in final storage 112, ideally in an airtight container. For the dried flower of cannabis or hemp botanical, the final volumetric dimension of the botanical is substantially the same as its initial volumetric dimension. Optionally, the resulting botanical may be further processed 112, such as having its oil extracted therefrom or it is trimmed such that the trimmed particles may be packed into cylindrical container for further use. This oil is extracted from the botanical by immersing the botanical in a solvent, such as food grade ethanol which is good to use for cannabis botanicals. The solvent is then distilled or boiled off, leaving behind the extracted oil. The extracted oil can be stored in capsule form or converted into pill form by adding a pill powder mix such as corn starch to the extracted oil and subjecting the resulting mixture to a standard pill pressing machine. Additionally, the dried botanical can be converted to small particles or powder form and packed into cylindrical containers for future use.

Figure 2:
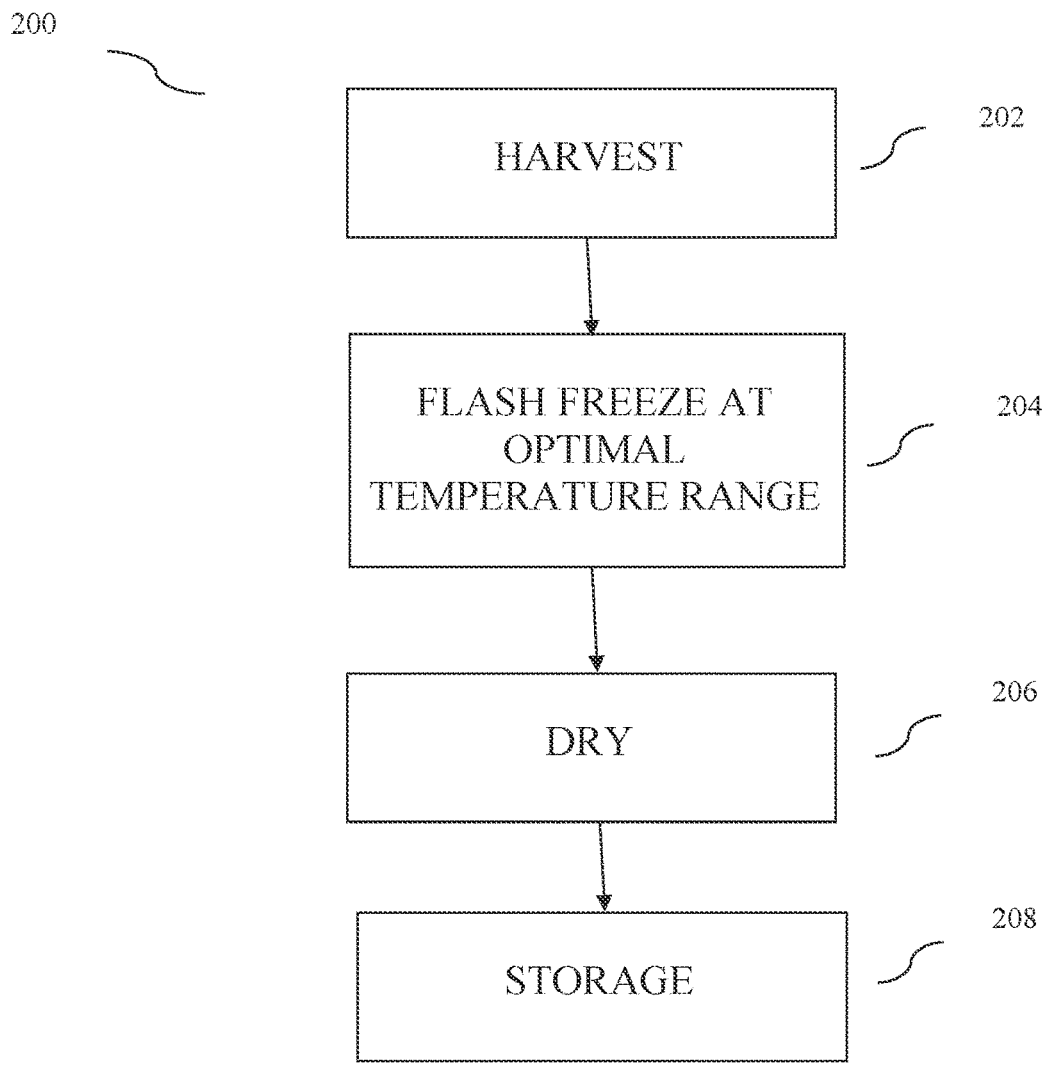
FIG. 2 is a flow chart summarizing a method of optimizing flash freezing process in drying botanicals, according to an embodiment.

Turning attention to FIG. 2, a second example of drying botanicals will now be described. Method 200 includes many similar or identical features to method 100. Within hours of harvesting 202 the botanical, it is placed in a freezer, ideally within one hour. For the step of flash freezing 204, the freezer should be at within the optimal temperature range of −45 f to −55 f. The lower temperature insures the botanical freezes as quickly as possible for best preservation. After removal, the flash frozen botanical is dried 206. This process includes placing the botanical in a drying machine, such as a lyophilizer which is generally composed of a vacuum chamber and a vacuum pump. Once the botanicals are placed in the vacuum chamber, the drying machine will lower the air pressure in the chamber and cycle the temperature. This process will allow the botanical to reach the triple point, where the frozen water molecules in the botanical will be sublimated or vaporized and turned into gas. This machine removes the gas from the vacuum chamber using the vacuum pump. The botanical is then removed, being dry and fully intact and can be stored 208, ideally in an airtight container.

Figure 3:
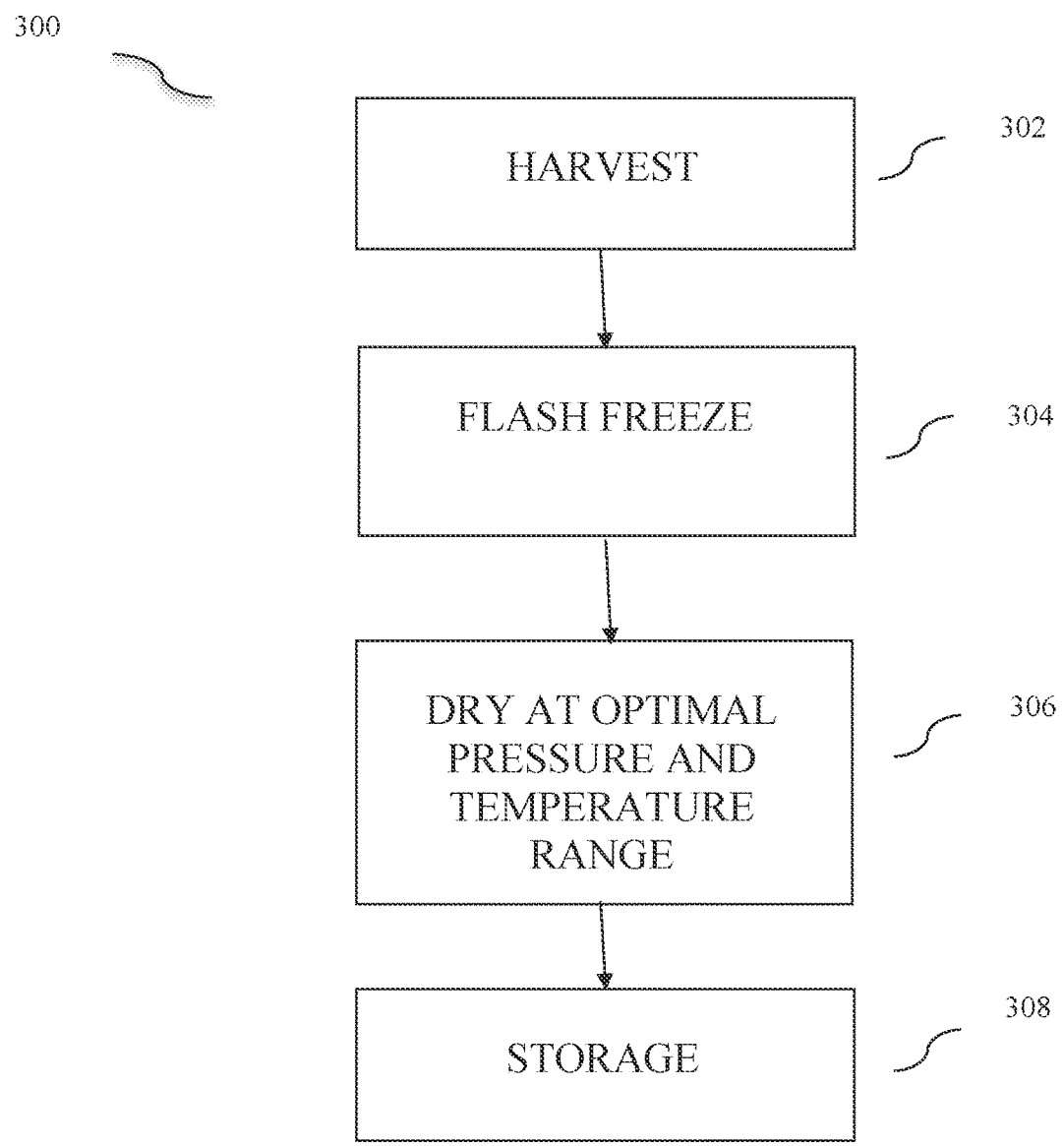
FIG. 3 is a flow chart summarizing a method of optimizing sublimation processing in drying botanicals, according to an embodiment.

FIG. 3 illustrates a third example of drying botanicals. Method 300 includes many similar or identical features to method 100. Within hours of harvesting 302 the botanical, it is placed in a freezer, ideally within one hour. For the step of flash freezing 204, the freezer should be as cold as possible, with the current range between −10 degrees Fahrenheit and at least −60 degrees Fahrenheit. The lower temperature insures the botanical freezes as quickly as possible for best preservation. After flash freezing, the frozen botanical is dried 306. This process includes placing the botanical in a drying machine, such as lyophilizer which is generally composed of a vacuum chamber and a vacuum pump. Once the botanicals are placed in the vacuum chamber, the drying machine will lower the air pressure in the chamber to an optimal pressure, between 300 and 600 torr for example. Other pressures are also possible. Also, during this step 306, the machine will cycle the temperature, ideally between 40 and 60 degrees Fahrenheit. This process will allow the botanical to reach the triple point, where the frozen water molecules in the botanical will be sublimated or vaporized and turned into gas. The machine removes the gas from the vacuum chamber using the vacuum pump. The botanical is then removed, being dry and fully intact and can be stored 308, ideally in an airtight container.

Figure 4:
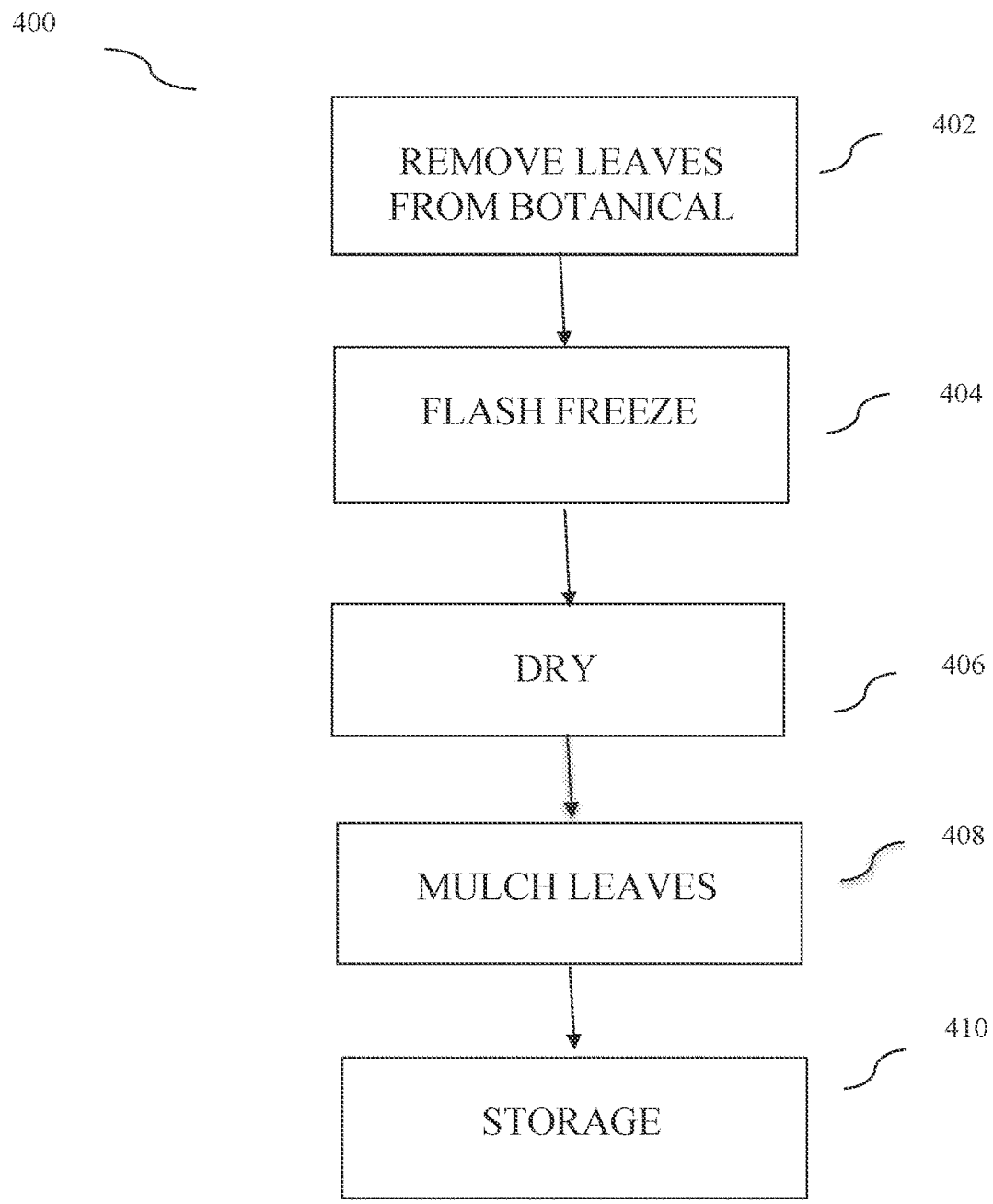
FIG. 4 is a flow chart summarizing a method of processing leaves of a botanical, according to an embodiment.

FIG. 4 illustrates an example of processing the leaves of a botanical. Method 400 includes many similar or identical features to method 100. Within hours of harvesting 402 the botanical, the leaves are separated from the botanical and then mulched. Alternatively, the leaves can be mulched at later steps in 400. The mulch is placed in the freezer, ideally within one hour from harvesting. For step of flash freezing 404, the freezer should be as cold as possible, with the current range being between −10 degrees Fahrenheit and at least −60 degrees Fahrenheit. The lower temperature insures the botanical freezes as quickly as possible for best preservation. After flash freezing, the frozen mulch is dried 406. This process includes placing the mulch in a drying machine such as a lyophilizer which is generally composed of a vacuum chamber and a vacuum pump. Once the mulch is placed in the vacuum chamber, the drying machine will lower the air pressure in the chamber and cycle the temperature. This process will allow the mulch to reach the triple point, where the frozen water molecules in the mulch will be sublimated or vaporized and turned into gas. The machine removes the gas from the vacuum chamber using the vacuum pump. The mulch is removed, being dry and fully intact. As indicated previously, the mulch can be first formed 408 after the leaves are flash frozen and dried (i.e., made substantially moisture free). The resulting dried mulched leaves can be stored 410, by packing the dried mulched leaves into a container, which may be cylindrically shaped, for future use.

The disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non-obvious combinations and sub combinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and sub combinations of the disclosed inventions that are believed to be novel and non-obvious. Inventions embodied in other combinations and sub combinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the invention described herein.

What is claimed is:

1. A method comprising:
   harvesting a cannabis botanical having flowers and leaves;
   separating the leaves from the botanical;
   flash freezing the leaves to solidify moisture content contained therein; and
   sublimating the solidified moisture content from the flash frozen leaves to form substantially moisture free flash frozen leaves.

2. The method of claim 1, further comprising the step of: forming a mulch from the moisture free flash frozen leaves.

3. The method of claim 2, further comprising the step of: packaging the mulch into at least one container.

4. The method of claim 1, further comprising the step of:
converting the sublimated moisture content to liquid form, said liquid form being comprised of water and terpene oil, said terpene oil being lighter in weight than said water.

5. The method of claim 4, further comprising the steps of:
separating said terpene oil from said water; and
collecting said separated terpene oil.

6. A method comprising:
harvesting a cannabis botanical having leaves and flowers;
separating the leaves from the botanical;
forming a mulch from the leaves;
flash freezing the mulch to solidify moisture content contained therein producing a flash frozen mulch; and
sublimating the solidified moisture from the flash frozen mulch to form a substantially moisture free flash frozen mulch.

7. The method of claim 6, further comprising the step of;
packaging the moisture free flash frozen mulch into at least one container.

8. The method of claim 6, further comprising the step of:
converting the sublimated moisture content to liquid form, said liquid form being comprised of water and terpene oil being lighter in weight than said water.

9. The method of claim 8, further comprising the steps of:
separating said terpene oil from said water; and
collecting said separated terpene oil.

\* \* \* \* \*